US012788382B2

(12) United States Patent
Bodenstein

(10) Patent No.: US 12,788,382 B2
(45) Date of Patent: Nov. 10, 2026

(54) APPARATUS AND METHODS FOR INTRA-CORPOREAL MANIPULATION AND DECOMPRESSION OF BODILY STRUCTURES

(71) Applicant: The Feinstein Institutes for Medical Research, Manhasset, NY (US)

(72) Inventor: Lawrence Bodenstein, New York, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 34 days.

(21) Appl. No.: 18/826,636

(22) Filed: Sep. 6, 2024

(65) Prior Publication Data

US 2025/0099091 A1 Mar. 27, 2025

Related U.S. Application Data

(60) Provisional application No. 63/539,669, filed on Sep. 21, 2023.

(51) Int. Cl.
*A61B 17/00* (2006.01)

(52) U.S. Cl.
CPC .. *A61B 17/00491* (2013.01); *A61B 17/00234* (2013.01); *A61B 2017/00004* (2013.01);
(Continued)

(58) Field of Classification Search
CPC .............. A61B 17/00; A61B 17/00491; A61B 17/00234; A61B 2017/00004; A61B 2017/00238; A61B 2017/00495; A61B 2017/005; A61B 2017/00862; A61B 2017/00951
See application file for complete search history.

(56) References Cited

U.S. PATENT DOCUMENTS 10,172,621 B2 * 1/2019 Machold ............... A61F 2/2451
2015/0351758 A1 * 12/2015 Shelton, IV ..... A61B 17/07292 606/219

OTHER PUBLICATIONS

Eiichiro Watanabe et al., Surgical technique to prevent spillage of cyst fluid during operation for cystic ovarian tumors, Pediatr Surg Int., Accepted: Jan. 23, 2013 / Published online: Feb. 9, 2013, pp. 645-649.

(Continued)

*Primary Examiner* — Vi X Nguyen
(74) *Attorney, Agent, or Firm* — Wissing Miller LLP

(57) ABSTRACT

A thin, flexible patch for decompressing a hollow structure, such as an ovarian cyst is applied to the hollow structure during a surgical procedure. The patch is adhered to the structure by an adhesive layer to form a fluid-tight seal with the structure. During the surgical procedure, such as a laparoscopic procedure, an aspiration needle is inserted through the patch and into the hollow structure with the patch forming a fluid-tight seal around the needle. Fluid is withdrawn by the aspiration needle, causing the structure to decompress and to be reduced in size. Once the structure is reduced in size it can be removed, for example, through a minimally invasive surgical port. The patch includes handles that facilitate grasping and manipulating the structure using laparoscopic instruments. The patch may also be formed by applying a curable material to the hollow structure and curing the material in situ so that it forms a patch that is adhered to the structure.

12 Claims, 9 Drawing Sheets

(52) U.S. Cl.
CPC ............... *A61B 2017/00238* (2013.01); *A61B 2017/0042* (2013.01); *A61B 2017/00495* (2013.01); *A61B 2017/005* (2013.01); *A61B 2017/00862* (2013.01); *A61B 2017/00942* (2013.01); *A61B 2017/00951* (2013.01)

(56) References Cited

OTHER PUBLICATIONS

Sadia Mobeen and Rad Apostol, Ovarian Cyst. [Updated Jun. 10, 2021]. In: StatPearls [Internet]. Treasure Island (FL): StatPearls Publishing; Jan. 2022.

Ki EY, Park EK, Jeong IC, et al. Laparoendoscopic Single Site Surgery for the Treatment of Huge Ovarian Cysts Using an Angiocatheter Needle. Yonsei Med J. 2019;60(9):864-869.

Terzic M, Aimagambetova G, Norton M, Della Corte L, Marin-Buck A, Lisón JF, Amer-Cuenca JJ, Zito G, Garzon S, Caruso S, Rapisarda AMC, Cianci A. Scoring systems for the evaluation of adnexal masses nature: current knowledge and clinical applications. J Obstet Gynaecol. Apr. 2021;41(3):340-347. (Available from: https://www.tandfonline.com/doi/full/10. 1080/01443615.2020. 1732892 ).

Kelleher CM, Goldstein AM. Adnexal masses in children and adolescents. Clin Obstet Gynecol. Mar. 2015;58(1):76-92. (Available from: https://journals.lww.com/clinicalobgyn/abstract/2015/03000/adnexal_masses_in_children_and_adolescents.8.aspx ).

American College of Obstetricians and Gynecologists' Committee on Practice Bulletins—Gynecology. Practice Bulletin No. 174: Evaluation and Management of Adnexal Masses. Obstet Gynecol. Nov. 2016;128(5): e210-e226. (Available from: https://pubmed.ncbi.nlm.nih.gov/27776072/ ).

* cited by examiner

Fig. 2A
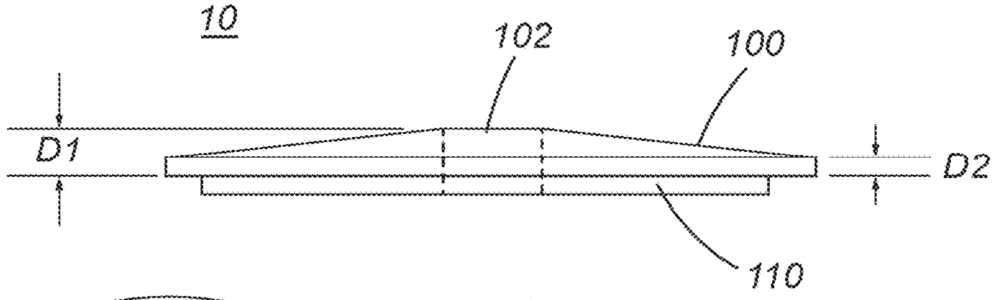
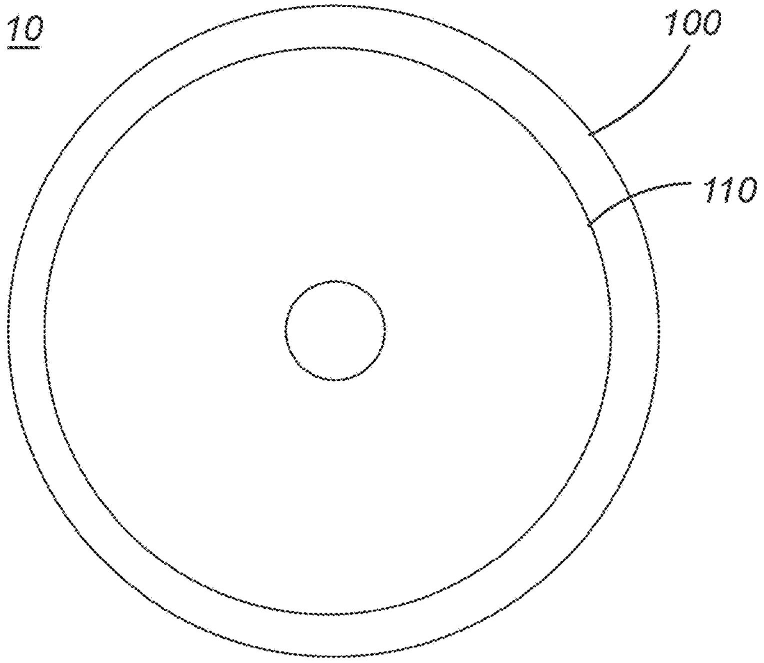
Fig. 2B
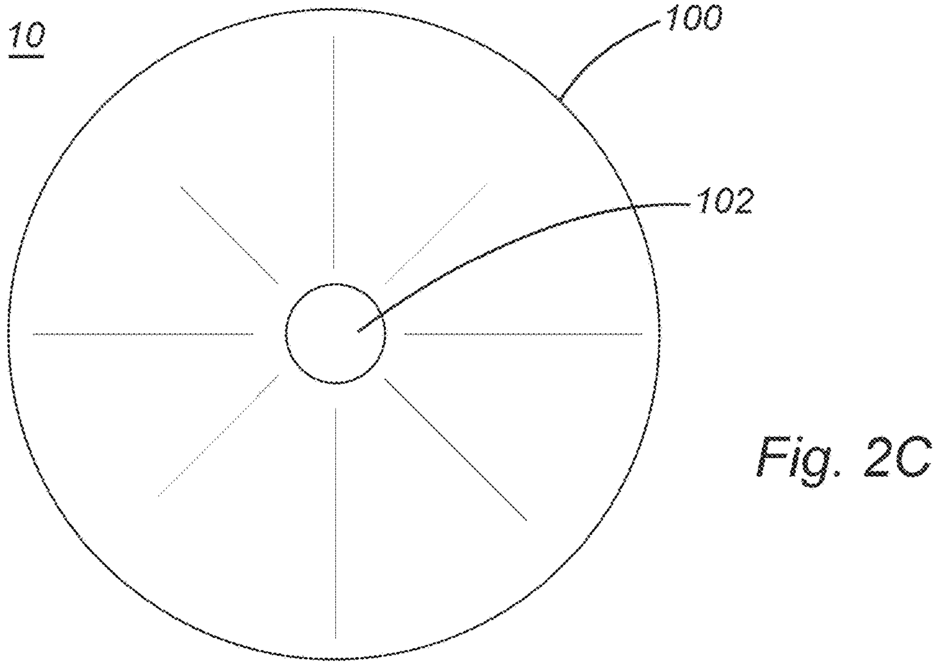
Fig. 2C

Fig. 5C
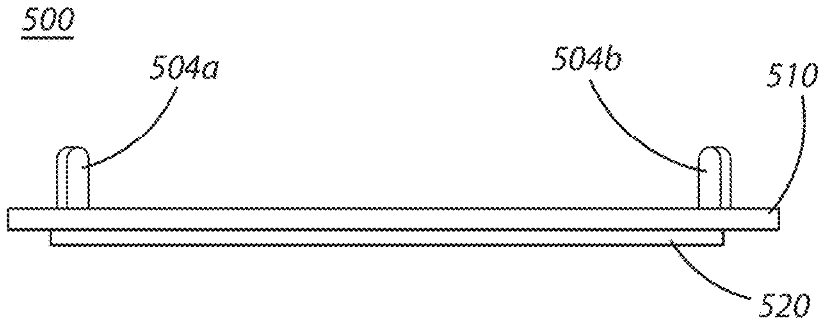
Fig. 5D
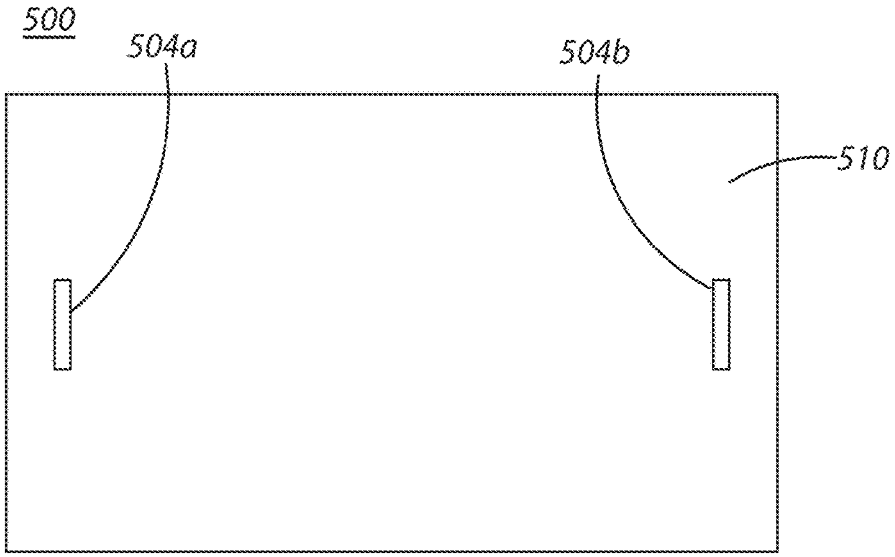
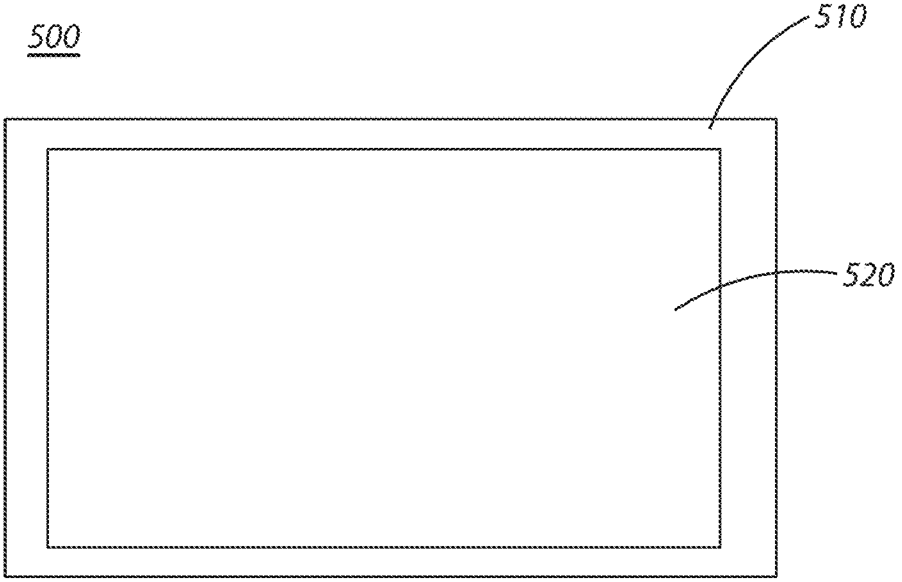
Fig. 5E

APPARATUS AND METHODS FOR INTRA-CORPOREAL MANIPULATION AND DECOMPRESSION OF BODILY STRUCTURES

CROSS-REFERENCE TO RELATED APPLICATIONS

The present disclosure is based on and claims benefit from U.S. Provisional Patent Application Ser. No. 63/539,669, filed on Sep. 21, 2023 entitled "Apparatus And Methods For Intra-Corporeal Manipulation And Decompression Of Bodily Structures" the contents of which are incorporated herein in their entirety by reference.

BACKGROUND

Field

This disclosure relates to apparatus for treatment of hollow structures and to methods for using such apparatus. In particular, this disclosure relates to apparatus for decompressing hollow structures while maintaining the integrity of the wall of the structure during a surgical procedure to prevent or reduce leakage of material from within the hollow structure. This disclosure further relates to apparatus and methods for intracorporeal manipulation of structures.

As used herein, the terms "hollow structure" or "hollow structures" refers to bodily structures with a cavity, which cavity may be filled with various fluids, such as a liquid or gas. Non-limiting examples of hollow structures include cysts, pseudocysts, hollow lesions, or hollow organs, such as the gallbladder, intestine, or blood vessels. Further, the terms "structure" or "structures" as used herein refers to any bodily structures including, but not limited to, hollow structures, solid (non-hollow) structures, lesions, and organs.

Minimally invasive surgery (MIS) allows resection of large structures through very small incisions. One difficulty often encountered is the need to remove a large structure from the body cavity once the structure has been dissected free. Benign hollow structures where there is little risk from contamination by fluid that may escape from within the structure can be cut into and removed piecemeal.

Where a hollow structure is suspected of being malignant and spillage of contents is to be avoided, one known technique is to introduce an impermeable bag through an incision. A malignant or possibly malignant structure can be placed in the bag using laparoscopic instruments and then removed piecemeal from the bag without contaminating the body cavity.

One subclass of hollow lesions are large cysts, for example ovarian cysts, which generally are benign but may in some cases be malignant, the distinction not being certain prior to resection. Violation of the cyst wall is to be avoided because of this malignant potential. These cysts can be dissected free from surrounding tissues using MIS techniques. However, to remove such large cysts intact requires a large incision.

One known technique is to use a modest incision, larger than MIS but smaller than the size of the object. A plastic bag is then glued to the surface of the cyst and the cyst decompressed (fluid drained) working within this isolating bag to prevent body cavity contamination (Watanabe, et al., 2013, Pediatric Surgery International, 29:645-649). In practice, this approach suffers from two drawbacks. First, it still requires a larger than MIS incision to securely glue the bag to the cyst, this being done by open technique. Second, although elegant in theory, in practice failure to obtain a secure seal can lead to significant contamination. If the cyst fluid can be evacuated without contamination of the body cavity, removal may be accomplished through MIS-size incisions (compare inflated to deflated balloon). Even if the cyst were to be approached via open (non-MIS) techniques, the required incision could be made much smaller.

There is a need for apparatus and methods to drain hollow structures intra-corporeally without spillage of contents. This not only would allow for extraction of a hollow structure after it has been dissected free but also may aid in the initial dissection of very large cysts or other structures. Dissection of large structures can be awkward using known MIS techniques, or even known open techniques unless a large incision is made.

SUMMARY

The present disclosure relates to apparatus and methods to treat patients with cysts and other fluid-filled hollow structures using MIS techniques and/or small incisions. The disclosed apparatus provides a practitioner with access to the interior of the structure to evacuate fluid from within the structure without allowing the contents of the structure to contaminate surrounding tissues and body cavities. Evacuation of the fluid reduces the size of the structure, allowing even very large hollow structures to be removed using MIS techniques.

According to one aspect of the disclosure the apparatus includes a small patch of flexible, fluid-impermeable material. The patch is adhered to the surface of a hollow structure through an MIS incision. The material forming the patch allows for needle puncture but is sufficiently resilient that it reseals after the needle is removed. Before or after the hollow structure has been dissected free, the practitioner inserts a needle connected with an aspirator through the patch and withdraws sufficient fluid from the structure to reduce its size so that it can be removed through the MIS incision. According to one embodiment, a portion of the patch forms a septum to form a seal around a needle inserted through the patch and that reseals when the needle is withdrawn. According to another embodiment, a septum is formed by a component embedded in or attached to the surface of the patch.

According to another aspect of the disclosure, the apparatus is used to withdraw fluids including both liquids and gases (e.g., air) from a fluid-filled structure. While most cysts are filled with liquid, lung cysts (and some other structures) may be filled with gas, or a mixture of gas and liquid. The disclosed apparatus includes embodiments adapted to facilitate the removal of such fluids.

According to another aspect, the patch includes one or more tabs or handles protruding from the surface opposite from the surface adhered to the hollow structure. The tabs are shaped to be grasped by surgical manipulators so that the practitioner can move the hollow structure as necessary during a surgical procedure. According to a further aspect, the tabs are used to secure traction sutures used to position the structure. According to a further aspect, a patch with such tabs may be applied to organs or structures other than hollow structures to facilitate surgeries on those other structures.

According to another aspect, an adhesive adheres the patch to a structure. According to one aspect, the adhesive is applied to the patch during manufacturing and a protective, peelable layer covers the adhesive. At the time of use, the practitioner peels off the layer, exposing the adhesive. The patch is then applied to the surface of the structure. Fluid may be drained from a hollow structure by a needle inserted through the patch. According to another aspect, an adhesive is applied to a patch and/or the structure by the practitioner at the time of use. According to a still further aspect, the adhesive is formed from multiple components that are mixed and applied to the surface of the patch and/or the structure at the time of use. The adhesive components are selected to cause the patch to adhere to the structure after a selected period of time. According to a still further aspect, the adhesive is curable by input of energy, for example, ultraviolet light. The patch, including a layer of uncured adhesive, is applied to the structure. The practitioner then applies energy, for example, using an ultraviolet light source, to cure the adhesive to fix the patch to the structure.

According to another aspect, the patch is formed from a flexible material that readily conforms to the shape of a hollow structure while fluid is drained from the structure. According to a further aspect, the patch has a non-uniform thickness being relatively thinner near the periphery of the patch. A thin peripheral portion may maintain better, more fluid-tight contact with the surface of the hollow structure during aspiration and decompression.

According to another aspect, the patch includes a central septum adapted to accept insertion of a hollow needle and to resiliently reseal when the needle is withdrawn. The patch, including the septum, may be formed from a variety of materials including rubber, silicone, and other medically suitable polymers and elastomers. For example, the patch may be formed from, or incorporate the material used to form the puncturing surface of implantable vascular access devices.

According to a further aspect, the patch can be made from a variety of materials and is not limited to materials that can safely remain implanted in a patient's body. Because the patch is removed if the structure is extracted, the patch may be present in the patient's body for a short period of time. Thus, materials may be selected for optimal mechanical properties, for example, low modulus of elasticity to allow the patch to remain attached to the surface as a hollow structure shrinks and the wall wrinkles.

According to a further aspect, there is provided a method and apparatus for treating hollow structures where a curable material provided as a liquid, a semisolid, a putty, a gel, a paste, or the like is applied to the surface of the hollow structure. The material includes chemical components that cause the material to form a solid or partially solid body adhered to the surface of the hollow structure after it is applied. The curable material is selected to form an elastomeric patch on the surface of the hollow structure. According to one aspect, the practitioner accesses the surface of the hollow structure, for example, via an MIS incision. The practitioner applies the curable material to a selected area of the surface of the hollow structure, for example, a 2-3 centimeter ("cm") diameter circular area. The practitioner causes the curable material to cure, forming an elastometic patch on the surface of the hollow body. The properties of the curable material are selected so that, when cured, the resulting elastomer adheres to the surface to form a liquid-tight bond. The properties of the elastomer are also selected so that, when pierced with a hollow needle or thin cannula, the elastomer forms a liquid-tight seal with the surface of the needle or cannula, and when the needle or cannula is removed the elastomer closes to form a liquid tight seal, preventing contents of the hollow structure from leaking.

According to one aspect, the curable material is cured by applying energy, for example, heat or light with a selected wavelength, once it has been applied to the hollow structure. According to a further aspect, the practitioner applies the material to the structure and then exposes the material to light, for example ultraviolet light with a wavelength of about 365 nanometers (nm), or to a heat source such as from the light emitted by a laparoscopic telescope.

According to one aspect, the intensity and/or duration of energy applied to cure the material is limited so that only a surface layer of the material is cured, leaving material below that surface in an uncured, or partially cured state. Such a configuration may be advantageous because the uncured or partially cured material may flow to form a liquid tight seal with the needle or cannula inserted into the hollow body. The uncured or partially cured material may flow to "heal" any opening in the patch once the needle or cannula is removed. According to one aspect, the practitioner removes the needle or cannula and applies additional energy to further cure the material to assure that any opening created by the needle or cannula is closed by cured elastomer. Alternatively, once a needle or cannula has been inserted into the hollow structure, additional energy or heat is applied to fully cure the material with the needle or cannula in place, thus fixing the needle or cannula within the patch.

According to another aspect, the curable material is cured by a curing agent, for example, a chemical agent that causes cross linking of polymer molecules or other chemical reactions, to cure the material into the elastomer. According to yet another aspect, the curable material is formed by a two-component chemical system. The practitioner mixes the components at the time the material is applied to the hollow structure. Once applied, the mixture cures to form the elastomer. The components may be provided in a syringe equipped with a mixing tip or other suitable mechanism that allows the practitioner to extrude and mix the components as they are applied to the hollow structure.

According to one aspect, the curable material is an elastomeric polymer or rubber compound that can be delivered as a paste.

According to another aspect, the curable material is a room temperature vulcanizing (RTV) or a rapid curing, silicone-based adhesive rubber or a composite resin including a silane or siloxane backbone with a bound organic moiety, such as methyltriacetoxysilane, a bis-amino silane such as bis(trimethylsilylpropyl)amine, methyl hydrogen polysiloxane, or vinyl oximino silane.

According to another aspect, the curable material is a gel-like acrylic-based composite, where the acrylic may be sobornyl acrylate, may be mixed with elastomeric or polymeric thickeners, and which may be cured by UV light. According to one aspect, the curable material is a gel-like composite. The practitioner applies the composite to the hollow structure and then delivers a brief pulse of UV light (e.g., about 1-2 sec) to produce a firm cured surface layer leaving the bulk of the curable material gel-like but confined within the surface layer. One or more additional applications of UV light may then be applied as the needle or cannula is removed, or immediately thereafter, to completely solidify the curable material. As above, the needle or cannula may also be left in place and fixed in position with additional curing. According to a further aspect, the curable material is a cyanoacrylate-based composite, where the cyanoacrylate may be ethyl 2-cyanoacrylate, or an ethyl/octyl monomer combination for added flexibility, and where curing is accelerated by a specific activator, such as an organic disulphide or sulfenamide.

According to another aspect, prior to applying the curable material that will form a patch on the hollow structure, a layer of adhesive is applied so that the adhesive is positioned between the structure and the patch. Such an arrangement may reinforce the bond between the patch and the surface of the structure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 2A, 2B and 2C show an edge-on view, a distal-side view, and a proximal-side view, respectively, of a patch for decompressing hollow structures during a surgical procedure according to a further embodiment of the disclosure;

FIGS. 5A to 5E show a patch adapted to facilitate manipulation of a structure during a surgical procedure according to a further embodiment of the disclosure;

DETAILED DESCRIPTION

As used herein, the term "distal" refers to the direction toward a structure being treated using patch 10 according to embodiments of the disclosure. The term "proximal" refers to the direction away from the structure being treated and towards a practitioner manipulating patch 10 to treat the organ.

Figure 1A:
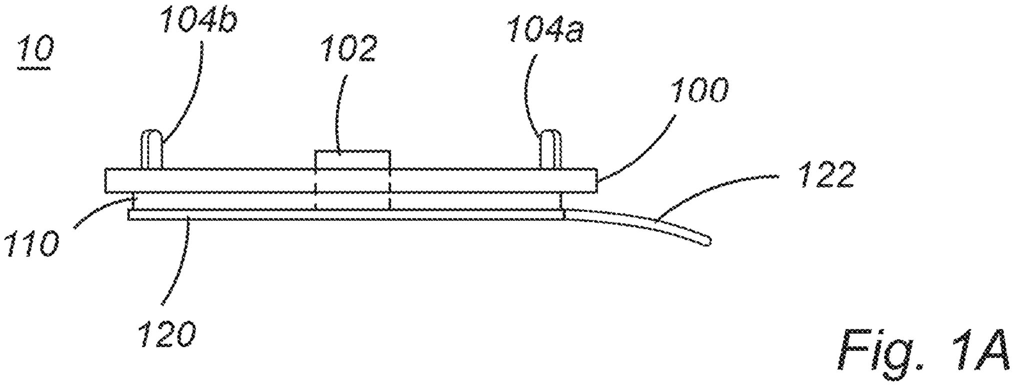
FIGS. 1A, 1B, and 1C show an edge-on view, a distal-side view, and a proximal-side view, respectively, of a patch for decompressing hollow structures during a surgical procedure according to an embodiment of the disclosure.
Figure 1B:
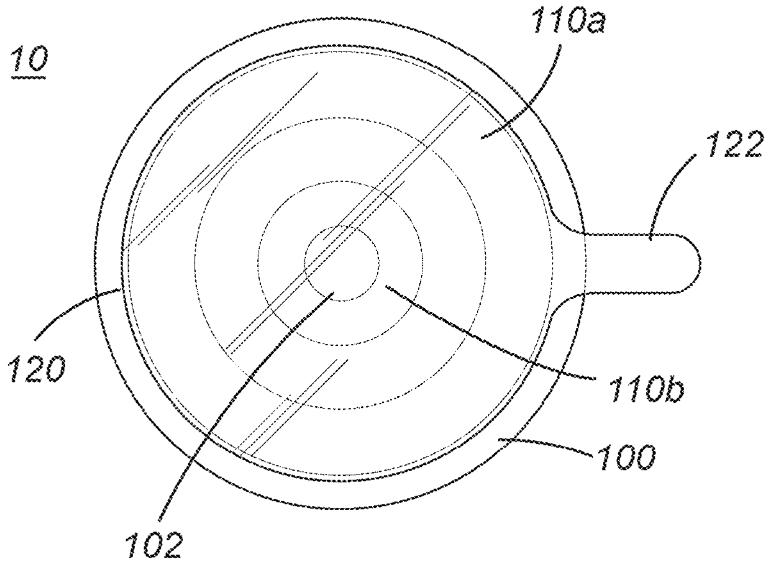
Figure 1C:
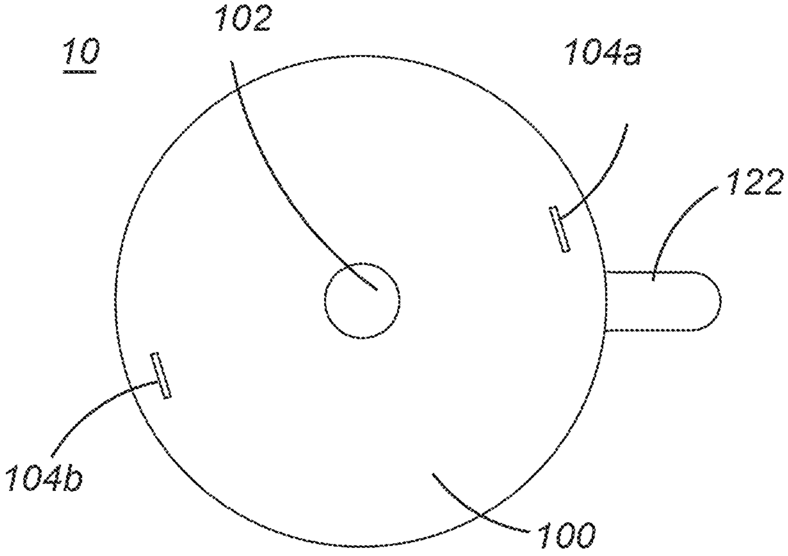

FIGS. 1A, 1B, and 1C show a patch 10 according to an embodiment of disclosure. FIG. 1A shows the patch edge on. FIG. 1B shows the distal, tissue-contacting side of patch 10. FIG. 1C shows the proximal side of patch 10. Patch 10 includes a flexible, fluid impermeable main body 100. According to one embodiment, main body 100 is formed from a biologically compatible polymer suitable for contacting internal structures of a patient being treated using patch 10. Suitable polymers include polyurethane elastomers, silicone elastomers, polypropylene, polyethylene, and the like. According to another embodiment, patch 10 is formed from bioabsorbable materials including polymers that can remain in the body of a patient after a procedure is complete and that will dissolve or be absorbed over time. Suitable polymers for such an absorbable patch 10 include polyglycolic acid, polyglactin 910, polydioxanone, and the like. According to another embodiment, patch 10 is composed of materials that are bio-compatible and/or inert and can be left in the body of a patient. According to another embodiment, the material forming main body 100 is any material with suitable mechanical characteristics, as will be described below.

According to one embodiment, main body 100 includes a septum 102. Septum 102 is shown at the center of a circular main body 100 in FIGS. 1A to 1C. Other shapes of main body 100 can be used with the scope of the disclosure. For example, main body 100 may be square, oval, rectangular, hexagonal, star-shaped, or the like. According to one embodiment, main body 100 is designed to be shaped by a practitioner at the time of use by trimming main body 100 to a selected shape at the time of use. Likewise, septum 102 can be placed at different locations than the center of main body 100. According to one embodiment, septum 102 is formed from the same material and is contiguous with the material forming main body 100. According to another embodiment, septum 102 is formed separately from main body 100 and affixed to a surface of main body 100. According to a further embodiment, septum 102 is formed separately from main body 100 and joined with main body 100 by co-injection molding.

Septum 102 allows a hollow needle or cannula, such as a needle connected with an aspirator, to be inserted through main body 100 and forms a fluid-tight seal around the needle. Septum 102 may also be self-healing so that, when the needle or cannula is withdrawn from the septum, the septum closes around the opening created by the needle or cannula to maintain main body 100 as fluid impermeable. According to one embodiment, main body 100 is formed from a material with mechanical properties and dimensions suitable to function as a septum 102, so that any portion of main body 100 function as a septum to form a fluid-tight seal with a needle or cannula inserted therethrough. According to one embodiment, septum 102 and/or main body 100 is formed from a silicone elastomer and has a thickness of about 2-5 mm. According to a further embodiment, the entirety of main body 100 is formed from a material suitable for forming a septum 102 and has a uniform thickness of about 2-5 mm.

As shown in FIG. 1A, patch 10 includes an adhesive layer 110 on the distal side thereof. According to one embodiment, adhesive layer 110 includes a contact adhesive that adheres to biological membranes such as a cyst wall, for example, of an ovarian cyst, when main body 100 is pressed onto the membrane. Adhesive layer 110 surrounds a central region of main body 100 that includes septum 102. As shown in FIG. 1B, according to one embodiment, adhesive layer 110 is comprised of a plurality of rings 110*a*, 110*b* that encompass septum 102. Adhesive layer 110 is selected to produce a water-tight seal and act quickly (seconds to several minutes) to adhere to the surface of a structure to be treated or manipulated.

According to embodiments where adhesive layer 110 includes a contact adhesive, layer 110 is initially covered with a removable protective sheet 120. Sheet 120 prevents patch 10 from unintentionally adhering to surfaces or becoming contaminated before it is deployed. Protective layer 120 may include tab 122 extending beyond a periphery of the patch. Tab 122 may be shaped to facilitate removable of protective layer 110 using laparoscopic instruments so that adhesive layer 110 can be uncovered after patch 10 has been introduced into a patient's body cavity, as will be explained below.

According to another embodiment, adhesive layer 110 includes chemical precursors that can be cured at the time of use to create an adhesive bond with the surface of structure. According to one embodiment, adhesive layer 110 is formed by chemicals that are activated by the application of energy, such as by light of a suitable wavelength, for example, ultraviolet light. According to one embodiment, such chemical precursors are applied by a practitioner at the time of use (e.g., during a surgical procedure). Patch 10 is then introduced into the patient's body cavity and manipulated into contact with the structure to be treated. A light source (not shown) is then used to cure the precursors, thereby bonding main body 100 to the structure. To facilitate curing, the material forming main body 100 may be selected to be transparent or translucent to the light.

According to another embodiment, adhesive layer 110 is formed by chemical precursors that react with one another to create an adhesive bond by a spontaneous chemical reaction. For example, a two-component glue may be used to form layer 110. According to one embodiment, a first chemical precursor may be applied to the distal side of main body 100 when patch 10 is manufactured. A practitioner applies the second component at the time of use and then positions the patch onto the structure to be treated. Alternatively, the second component may be applied to the structure prior to placement of the patch. Once the reaction between the first and second chemicals has occurred, patch 10 will be bonded to the surface of the structure.

According to another embodiment, adhesive layer 110 is formed from one or more of adhesives based on fibrin, for example, Tisseel™, CrosSeal™, Evicel™, Hemaseel™, Bolheal™, or TachoSil™, adhesives based on collagen, for example, FloSeal™ or Surgiflo™, adhesives based on gelatin, for example, GRF (gelatin, resorcinol, formaldehyde) or GRFG (gelatin, resorcinol, formaldehyde, glutaraldehyde), adhesives based on albumin, for example, BioGlue™ or ProGel™, adhesives based on chitosan, for example, HemCon™ or ChitoFlex™ adhesives based on dextran, for example, Actamax™, adhesives based on chondroitin sulfate, UV-cured adhesives, polycyanoacrylate adhesives, for example, Histoacryl™, Dermabond™, Octylseal™, Surgiseal™, Omnex™, Indermil™, Liquiban™, Histoacryl™, Histoactryl Blue™, Glubran™, Glubran2™, or IFABond™, adhesives based on polyethylene glycol, for example, CoSeal™, FocalSeal-L™, DuraSeal™, CoSeal™, or Spray-Gel™, adhesives based on polyurethane, for example, TissuGlu™, dendrimer and hyperbranched adhesives, for example, OcuSeal™ or Adherus™, adhesives based on hydrogels including electrostatic or charged hydrogels, and mussel-based or gecko-based biomimetic adhesives.

FIG. 1B shows adhesive layer 110 comprised of two rings 110*a*, 110*b*. A greater or fewer number of rings of adhesive may be provided within the scope of the disclosure. According to another embodiment, instead of one or more rings 110*a*, 110*b*, adhesive layer 110 covers all or substantially all of the distal surface of main body 100. According to a further embodiment, adhesive layer 110 covers the distal surface of main body 100 except for the region adjacent to septum 102.

According to one embodiment, patch 10 includes one or more grasping handles or tabs 104*a*, 104*b*. Handles 104*a*, 104*b* are shaped to facilitate grasping of main body 100 by laparoscopic instruments. According to one embodiment, handles 104*a* 104*b* extend from the proximal surface of main body 100. According to another embodiment, in addition to, or instead of handles 104*a*, 104*b* extending in the proximal direction from the surface of patch 10, the handles extend from the peripheral edge of main body 100 in the plane of the main body. Two handles 104*a*, 104*b* are shown but a fewer or greater number of handles may be provided within the scope of the disclosure.

According to one embodiment, main body 100, including handles 104*a*, 104*b*, is attached to a patient's solid organ or structure, such as the liver or spleen, during a laparoscopic surgical procedure. In this case, handles 104*a*, 104*b* can be used to manipulate the structure during the procedure.

According to one embodiment, patch 10 has a diameter smaller than or equal to the diameter of a standard MIS umbilical port size of about 10-12 millimeters (mm). According to another embodiment, patch 10 is larger than an MIS umbilical port and, to introduce the patch into the patient, the patch is folded-over or rolled-up. According to a preferred embodiment, patch 10 has a diameter of between about 10 mm and about 300 mm. According to a more preferred embodiment, patch 10 has a diameter of between about 30 mm and 60 mm. According to another embodiment a patch that cannot be introduced through an MIS port is used in an open (non-MIS) procedure.

FIGS. 2A, 2B, and 2C show patch 10 according to another embodiment of the disclosure. As with previous embodiments, septum 102 is formed at the center of a circular main body 100. According to one embodiment, septum 102 is not a separate structure but is a region of main body 100 adapted to receive a needle or cannula. FIG. 2A is a side view of patch 10 showing how the thickness of main body 100 varies from the center to the periphery. According to this embodiment, the center of main body 100 in the region of septum 102 has a first thickness D1. Thickness D1 may be selected to facilitate sealing of the septum when it is pierced by a hollow aspirating needle. For example, thickness D1 may be about 2 mm to about 5 mm. The thickness of main body 100 is reduced toward the periphery. As shown in FIG. 2A, the thickness of the edge of main body is a second thickness D2. Thickness D2 may be selected to facilitate adhesion and the maintenance of a fluid-tight seal between the main body 100 and the structure being treated. Thinner material along the periphery and away from septum 102 may make main body 100 more pliable and better able to conform to wrinkles that may be created when the structure is decompressed, as will be explained below.

The profile of main body 100 in FIG. 2A shows a linear change in thickness along the radius of the main body. The disclosure is not limited to patches 10 with a linear change and includes embodiments where there is a step change in thickness along the radius, where the thickness changes by a plurality of steps along the radius, and where the thickness changes according to other functions of the radius.

FIG. 2B shows the distal, tissue-facing surface of patch 10. In this embodiment a single adhesive layer 110 is provided. According to one embodiment, adhesive layer 110 is not applied in the region of septum 102 in order to avoid having an aspiration needle pass through the adhesive layer when it is inserted into the structure being treated. According to another embodiment, adhesive layer 110 covers substantially all of the distal surface of main body 100, including the central region adjacent to septum 102.

Figure 3A:
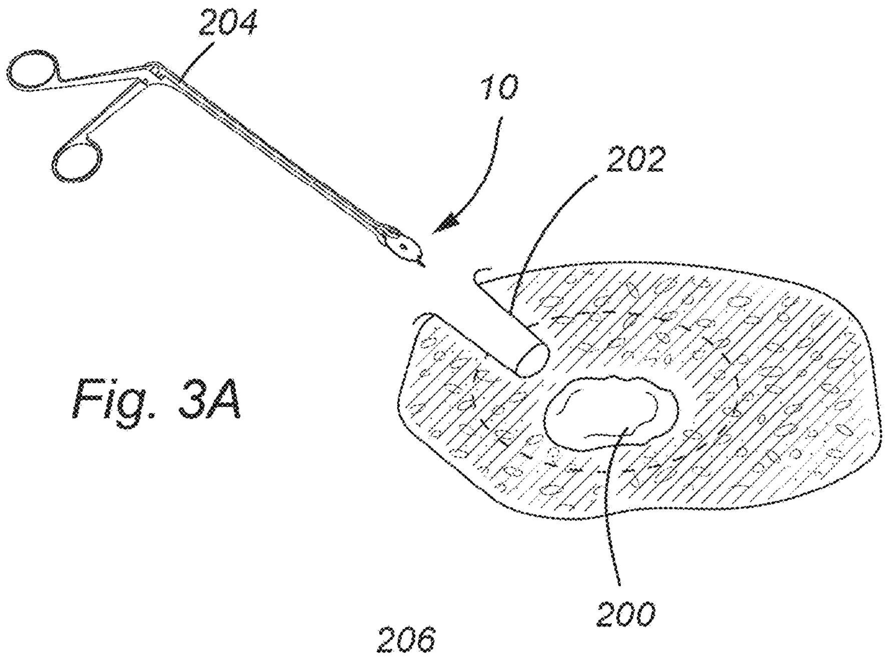
FIGS. 3A to 3E show steps for performing a surgical procedure using a patch according to embodiments of the disclosure.

FIGS. 3A to 3E show steps for using a patch 10 according to embodiments of the disclosure. These figures show a cross section of a patient's body that is undergoing a surgical procedure to treat a structure 200. Structure 200 may be an ovarian cyst or other fluid-filled structure that requires treatment. In cases where the structure is known or suspected to include malignant cells, it may be important that the contents of the structure do not escape the surrounding membrane as this could allow such cells to invade other parts of the body. As shown in FIG. 3A, an MIS port 202 is positioned through the patient's skin and into a body cavity, for example, the patient's pelvic cavity, using techniques known to those of skill in the field of the disclosure.

Structure 200, which may be an ovarian cyst that may include malignant cells, is accessed through port 202 using laparoscopic instruments.

In FIG. 3A, patch 10 is held by laparoscopic forceps 204 and inserted through port 202 into the pelvic cavity. Forceps 204 (and other laparoscopic instruments, not shown) are used by the practitioner to manipulate patch 10 to position main body 100 of patch 10 onto the surface of structure 200. According to one embodiment, forceps are used to remove protective layer 120 (see, e.g., FIG. 1A) to expose adhesive layer 110 while the patch is positioned in the pelvic cavity. According to other embodiments, before patch 10 is inserted through port 202, an adhesive and/or chemical precursors to an adhesive are applied by the practitioner to the distal surface of main body 100. Depending on relative sizes of patch 10 and port 202, the patch may be partially or completely folded or rolled up to fit through the port.

Figure 3B:
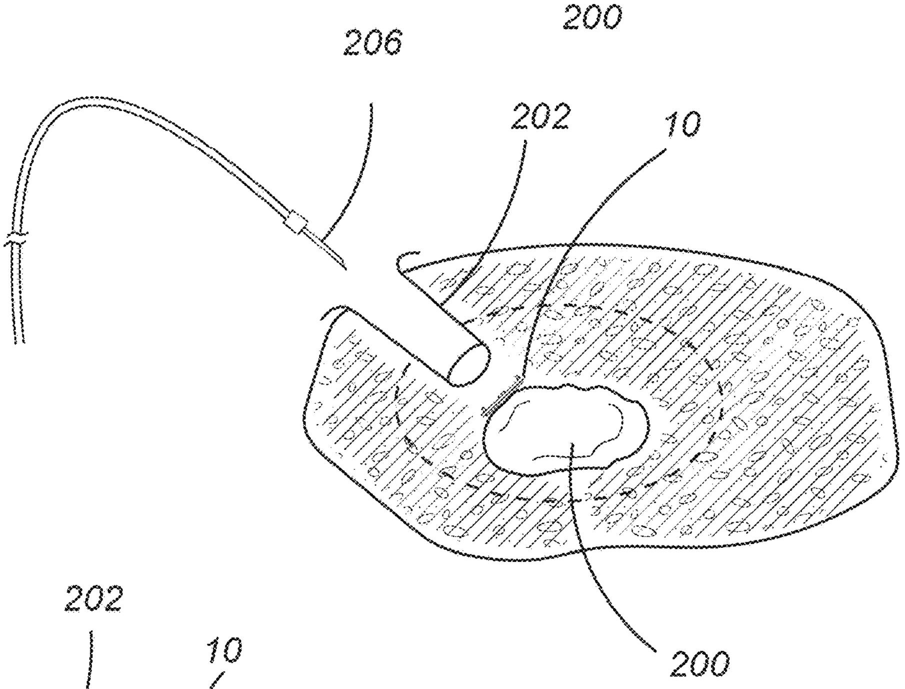

As shown in FIG. 3B, patch 10 is positioned on the surface of structure 200. At this point, the practitioner may visualize patch 10 and to assure that good contact is made between the patch and the structure. According to one embodiment, main body 100 is made from a transparent material, allowing the practitioner to see that an occlusive seal between the patch and the structure has been created. In the case where the adhesive is light-activated, a suitable light source is inserted through port 202 and energized to deliver energy to cure the adhesive.

The practitioner then dissects the structure from the surrounding tissue using techniques known in the field of the disclosure. In addition, the practitioner may use handles 104*a*, 104*b* to manipulate the structure during dissection. Using the handles to manipulate the lesion instead of grasping the structure directly may reduce the risk that a grasping instrument will puncture the structure wall or surface.

Figure 3C:
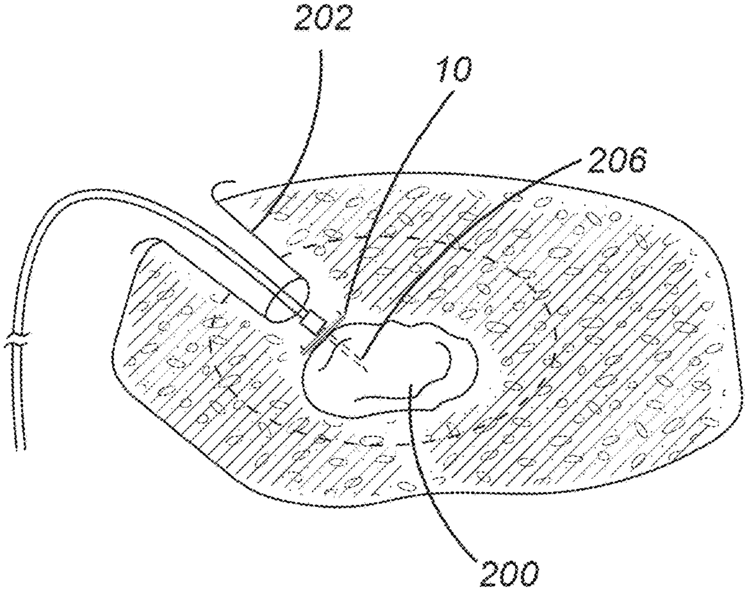
Figure 3D:
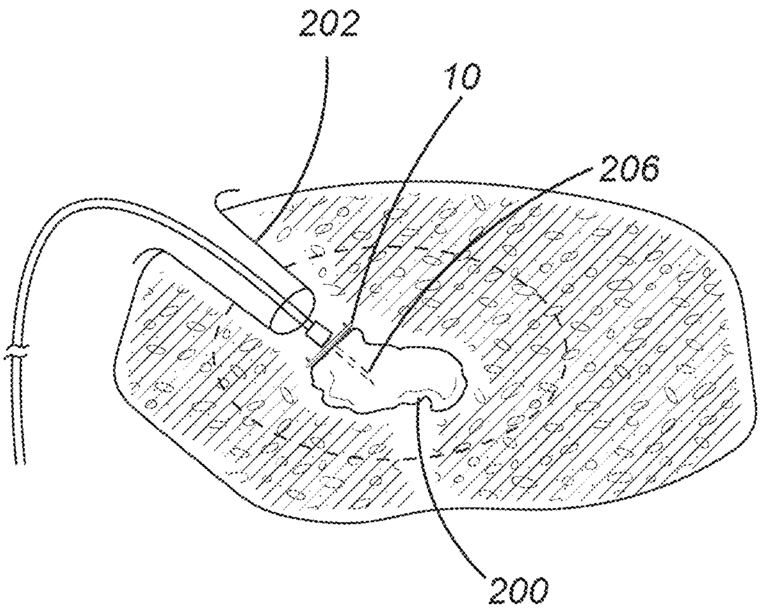

As shown in FIG. 3C, an aspiration needle 206 is inserted through port 202. Needle 206 is inserted through septum 102 of main body 100. Septum 102 forms a fluid tight seal with the outside surface of needle 206. According to one embodiment, needle 206 is a non-coring needle such as a Huber needle. This would allow the practitioner to insert needle 206 into septum repeatedly without coring the septum. According to another embodiment, needle 206 is a standard hollow needle. Once needle 206 is inserted into the hollow structure through septum 102, the practitioner actuates an aspiration mechanism (not shown) to withdraw fluid from the interior of structure 200. As shown in FIG. 3D, when fluid is withdrawn, the size of the structure shrinks. Aspiration may be continued until structure 200 is small enough to fit through port 202.

According to one embodiment, instead of inserting needle 206 through port 202, needle 206 is instead inserted through the abdominal wall into the pelvic cavity to access septum 102. According to one embodiment, such a needle may include a sheath or other protective covering that isolates the needle from the surrounding tissue once it is withdrawn from septum 102 to prevent exposing the surface of the needle (which has been in contact with fluid inside structure 200) to other tissues in the abdominal or pelvic cavity and possibly transferring malignant cells to other organs.

Figure 3E:
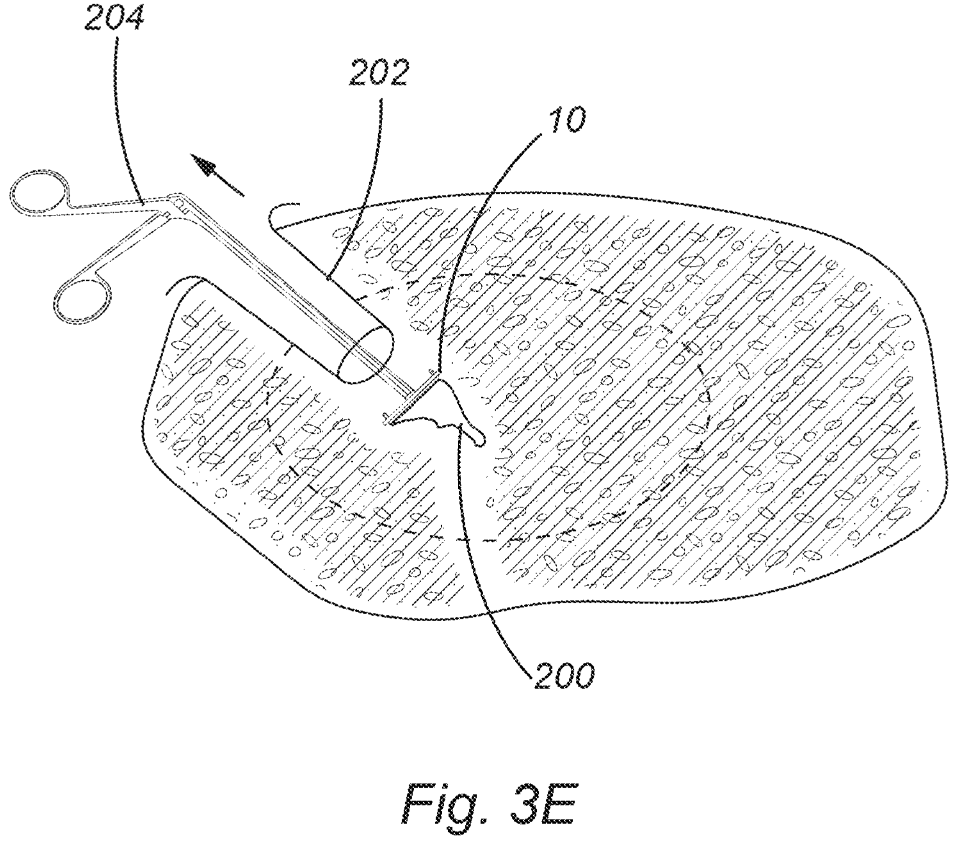

As shown in FIG. 3E, needle 206 is removed and forceps 204 are used to grasp decompressed structure 200 and to pull it from the pelvic cavity through port 202. According to another embodiment, the decompressed hollow structure with attached patch may be placed in a specimen retrieval bag prior to removal from the pelvic cavity.

Management of fluid-filled structures such as simple ovarian cysts with malignant potential are one embodiment of the present disclosure. Other embodiments are also within the scope of the disclosure. According to other embodiments, patch 10 is used to treat structures filled with gases (e.g. air) or mixtures of gas and liquid, such as a cyst of the lung. Patch 10, including handles 104*a*, 104*b*, may be used to provide one or more points of purchase on large solid structures that are not amenable to decompression including organs such as the spleen during a splenectomy.

According to other embodiments, instead of, or in addition to withdrawing fluid, patch 10 according to the disclosure can be used to allow additional fluid to be injected into a hollow structure. For example, to treat some diseases of the gallbladder it is necessary to perform a contrast study (cholangiogram). Known techniques for doing this generally require that the gallbladder be punctured with a needle and after the needle is removed the puncture site is closed with surgical clips. By using a patch 10 according to embodiments of the disclosure, insertion and removal of a needle during a cholangiogram may be simplified, since there is no need to close the puncture site. Thus, devices within the scope of the disclosure may simplify such procedures and reduce or eliminate leakage, which may include infected gallbladder contents.

Embodiments disclosed with respect to FIGS. 3A to 3E show patch 10 used in a pelvic laparoscopic surgical procedure. Use of patch 10 is not limited to pelvic laparoscopic procedures and can also be used in other body cavities such as the abdomen or thorax, in thoracoscopy as well as laparoscopy, and during open surgical procedures.

According to some embodiments, fluid is alternatively removed and added back to the cyst or other fluid-filled structure during a procedure. This may be done to adjust the size of the structure to aid in dissection, for example, when treating the gallbladder or to remove an ovarian cyst. According to one embodiment, once dissection is complete, the structure is decompressed sufficiently so that it can be removed via port 202, as shown in FIG. 3E.

Figure 4A:
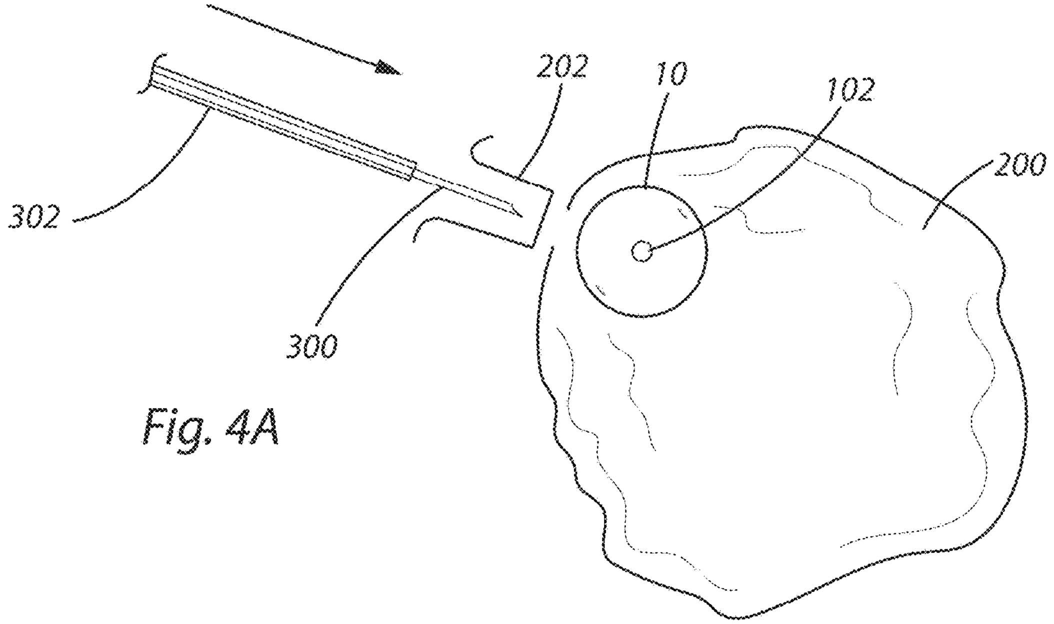
FIGS. 4A to 4C show steps for performing a surgical procedure using a patch according to a further embodiment of the disclosure.
Figure 4B:
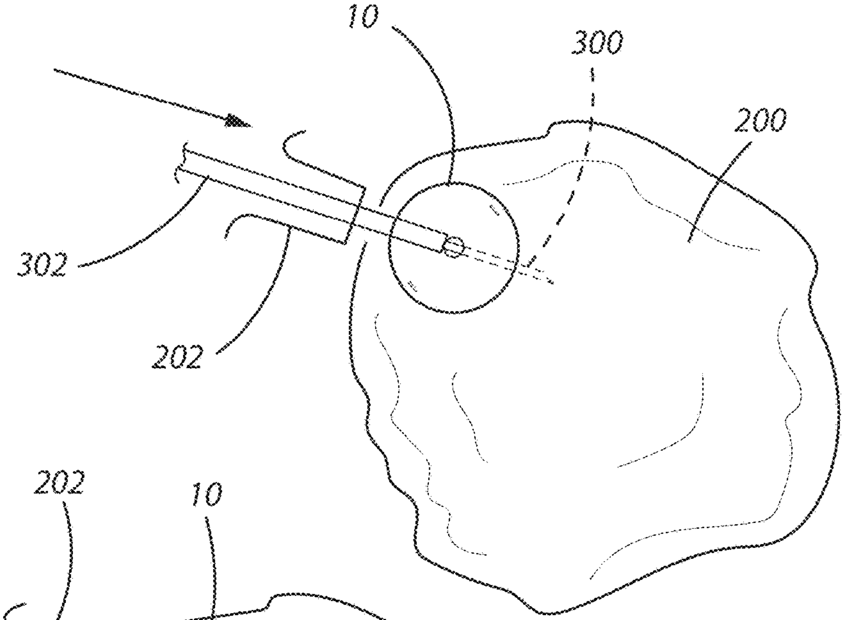
Figure 4C:
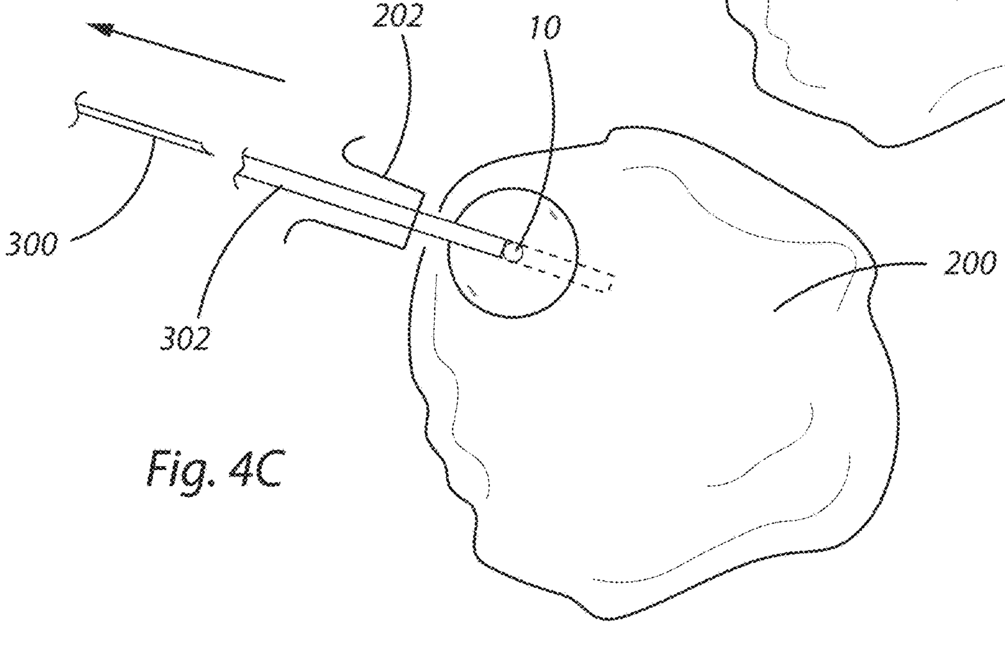

FIGS. 4A, 4B, and 4C show a further embodiment of the disclosure used to treat a fluid-filled hollow structure 200. In this embodiment, a catheter 302 is used to withdraw and/or deliver fluids from and to the structure. As shown in FIG. 4A, catheter 302 is fitted over trocar 300. Trocar 300 is selected to provide sufficient stiffness to the catheter to allow the catheter 302 and trocar 300 to be inserted through septum 102 of patch 10. Catheter 302 and trocar 300 are advanced through port 202. As shown in FIG. 4B, trocar 300 pierces septum 102 and both the trocar and catheter 302 are inserted into the structure. As shown in FIG. 4C, trocar 300 is withdrawn, leaving catheter 302 in fluid communication with the interior of the structure. To decompress structure 200, fluid is withdrawn by catheter 302.

According to another embodiment, patch 10 is used to facilitate delivering fluids into a hollow structure. For example, treatment of the gallbladder, the urinary system or the bowel may be facilitated by injection of a radiological contrast agent into the structure thereon. Once needle 206 or catheter 302 is inserted through septum 102 and into the structure, the agent is injected. According to one embodiment, needle 206 or catheter 302 is withdrawn prior to radiological imaging to provide an unobstructed view of the structure. Because septum 102 is self-sealing, once the needle or catheter is withdrawn, the fluid including the contrast agent is confined to the interior of the structure.

According to another embodiment of the disclosure, patch 10 is used to facilitate treatment of hollow structures by delivering a fluid including a therapeutic agent. For example, in treatment of parasitic cysts such as hydatid liver cysts, it is vital during surgery not to spill cyst contents within the body to avoid spreading infection to other organs or causing anaphylaxis. According to one embodiment, a portion of the cyst fluid is withdrawn, for example, as shown in FIG. 3D and then replaced with a therapeutic solution, such as an antiparasitic or antineoplastic agent. This procedure may be repeated, withdrawing fluid and injecting additional therapeutic fluids to fully treat the cavity. In another example, a sclerosing agent may be introduced after withdrawal of cyst contents to obliterate the cyst cavity.

Figure 5A:
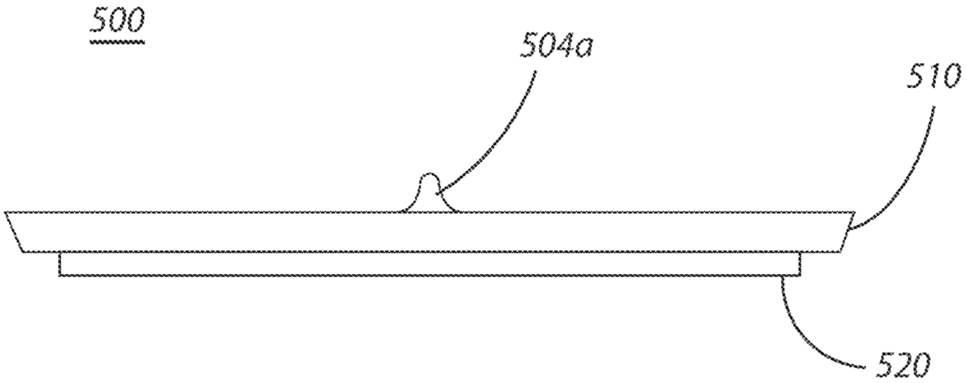
Figure 5B:
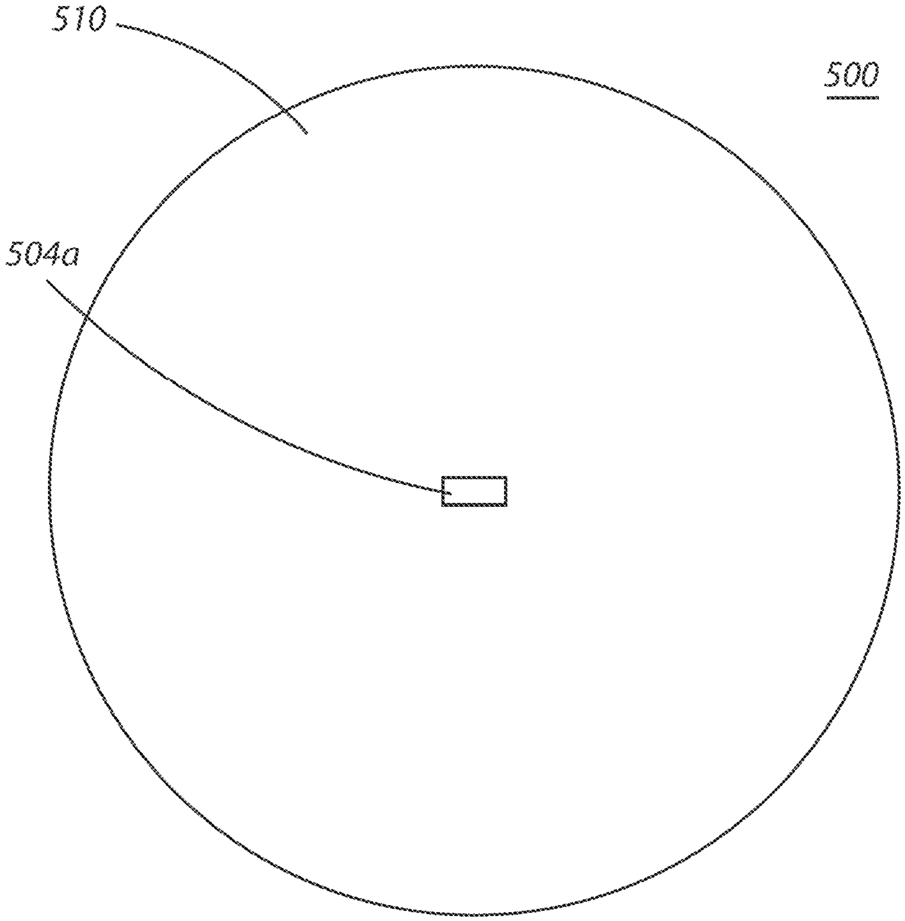

FIGS. 5A, 5B, 5C, 5D, and 5E show a patch 500 according to further embodiments of the disclosure that facilitates manipulation of a structure. Patch 500 includes one or more tabs or handles 504A, 504*b* shaped to be grasped by medical instruments, such forceps, clamps or minimally invasive manipulating instruments. FIG. 5A and FIG. 5B depict one embodiment of patch 500, which is round and has a tab or handle 504*a* at or near the center of the patch.

FIGS. 5C, 5D and 5E show another embodiment of patch 500 that is rectangular and has two tabs or handles (504*a*, 504*b*). Tabs 504*a*, 504*b* are connected with body 510. Body 510 is formed from a flexible material adapted to conform to the shape of the structure, as discussed with respect to the previous embodiments. According to a preferred embodiment, body 510 and/or tabs 504*a*, 504*b* are formed from a bioabsorbable polymer. A bioabsorbable adhesive 520 is applied to the surface of body 510 opposite from tabs 504*a*, 504*b*. As shown in FIG. 5E, adhesive 520 covers all, or substantially all of the surface of body 510. The disclosure is not limited to round or rectangular patches, and includes patches that are square, polygonal, or cut into a selected shape to conform to a specific organ or to facilitate a particular surgical procedure. Multiple patches may be applied at different locations on the structure as needed to aid in manipulation of the structure. According to another embodiment, a single, larger patch with multiple tabs or handles is used. The larger patch may distribute traction forces over a larger area of the structure and may decrease the likelihood of disruption of the surface of the structure. According to one embodiment, patch 500 is cut to a desired size and shape at the time of use, for example, by a medical practitioner prior to or during a surgical procedure.

In use, patch 500 is applied to the surface of a structure to be treated. Once adhesive 520 is cured so that body 510 is securely fixed to the lesion or organ, a medical practitioner uses tabs 504*a*, 504*b* to manipulate the structure. Because the forces applied to tabs 504*a*, 504*b* are distributed across the surface of the structure that is fixed to body 510, these forces are less likely to rupture the structure. Where the structure being treated will remain in the body after treatment, patch 500 remains adhered to the structure. Because tabs 504*a*, 504*b*, body 510, and adhesive 520 are bioabsorbable, these will be absorbed over time. According to other embodiments, patch 500 is not bioabsorbable and is removed with the structure during the treatment procedure.

Figure 6A:
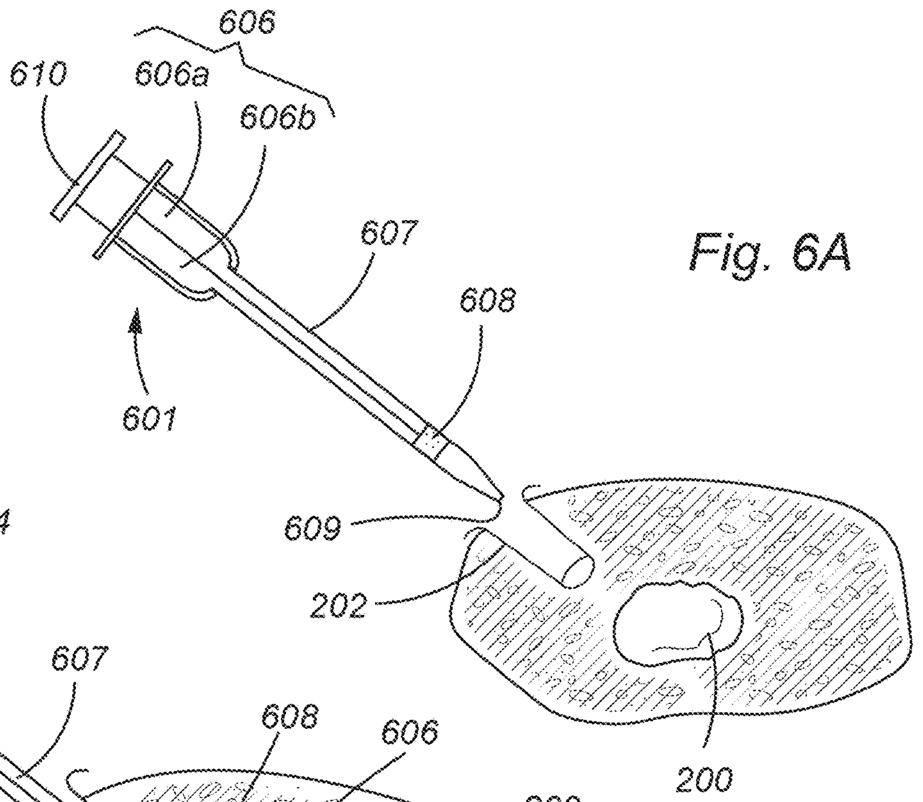
FIGS. 6A to 6C show steps for performing a surgical procedure using a patch according to another embodiment of the disclosure.
Figure 6B:
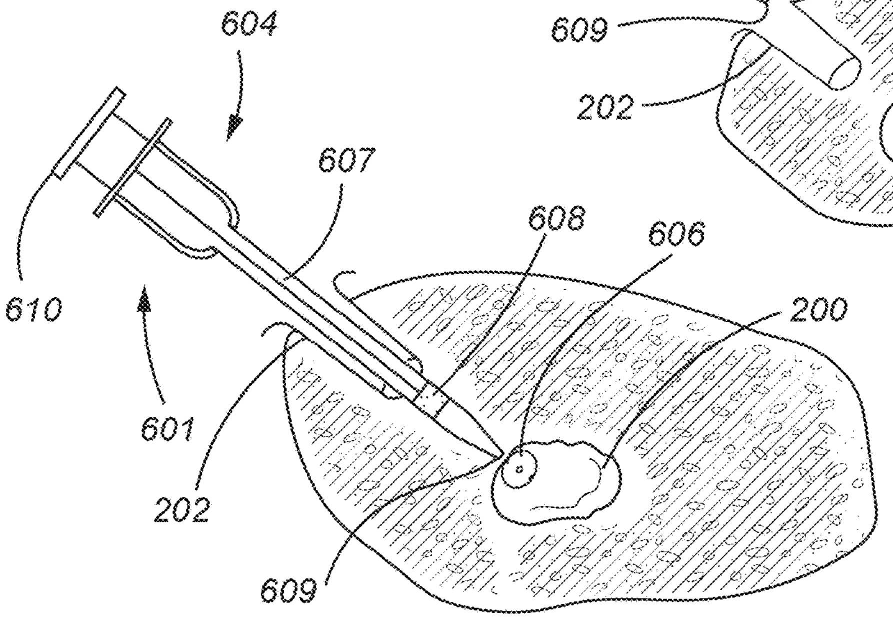
Figure 6C:
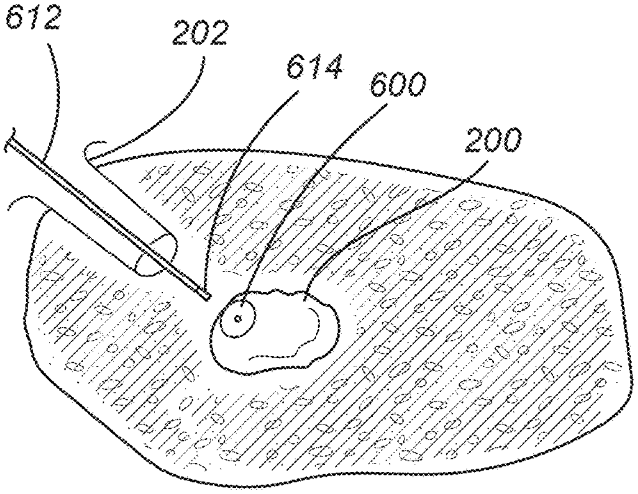

FIGS. 6A-6C show steps for treating a hollow structure 200 according to another embodiment of the disclosure. As in previous embodiments, MIS port 202 is provided to access a patient's body cavity that surrounds the hollow structure 200. According to this embodiment, curable material 606 is provided by delivery device 601, such as a syringe.

According to one embodiment, curable material 606 is formed by two precursors 606*a*, 606*b* held in a two-barrel syringe 601. Syringe 601 includes a delivery tube 607. Mixing device 608 forms part of tube 607, preferably near distal tip 609.

As shown in FIG. 6B, tube 607 is moved through port 202 until tip 609 is near or in contact with hollow structure 200. The practitioner actuates syringe 601 by pressing plunger 610 to displace precursors 606*a*, 606*b* along tube 607. Mixing device 608 causes the precursors to mix as they move along tube 607 and exit from tip 609. The mixed precursors 606*a*, 606*b* form the cureable material 606, which is applied to the surface of hollow structure 200.

The practitioner applies curable material 606 (that is in this embodiment, the mixed precursors 606*a*, 606*b*) to cover a selected portion of structure 200, for example, in a circular shape with a diameter of about 2 to 3 cm. The disclosure is not limited to a circular patch, and includes any shape and size selected by the practitioner, including round, oval, square, rectangular, polygonal, or star-shaped and the like. Precursors 606*a*, 606*b* may be components of a two-part silicone based adhesive rubber system where one precursor 606*a* includes a liquid, uncured silicone rubber and the other precursor 606*b* includes a curing agent that causes the rubber 606*a* to cure to form a solid, elastomeric patch 600 on the surface of structure 200.

According to further embodiments, elastomer 606 is formed from a room temperature vulcanizing (RTV) or a rapid curing, silicone-based adhesive rubber or a composite resin including, but not limited to a silane or siloxane backbone with a bound organic moiety to facilitate cross-linking and curing. The organic moiety may be selected from methyltriacetoxysilane, a bis-amino silane such as bis(trimethylsilylpropyl)amine, methyl hydrogen polysiloxane, or vinyl oximino silane or other suitable cross linking or curing agents known to those of skill in the field of the invention.

As disclosed in previous embodiments, once patch 600 is formed, a hollow needle or thin cannula 206 is inserted through the patch and into hollow structure 200 to decompress the structure and/or to deliver fluids or therapeutic agents to the structure. The elastomeric, rubber-like properties of patch 600 form a seal around the needle in a manner similar to the seal formed by septum 102 in previous embodiments. According to one embodiment, needle or cannula 206 can be withdrawn from structure 200. Elastomeric patch 600 closes around the opening left by the needle or cannula, preventing potentially harmful materials such as malignant cells from leaking out from the structure.

According to a still further embodiment, once needle or cannula 206 is withdrawn from structure 200, an additional layer of curable material 606 is applied to patch 600 and then cured to assure that any opening left by withdrawal of the needle is fully closed. The additional layer may extend beyond the periphery of patch 600 to enhance the seal between the patch and the surface of structure 200. According to a still further embodiment, the additional layer is formed from a different material than curable material 606. For example, curable material 606 forming patch 600 may be a two-component silicone rubber. Once needle or cannula 206 is withdrawn, an additional layer of cyanoacrylate adhesive is applied to patch 600 to assure any opening is sealed and/or to enhance adhesion of patch 600 with structure 200.

Figure 7A:
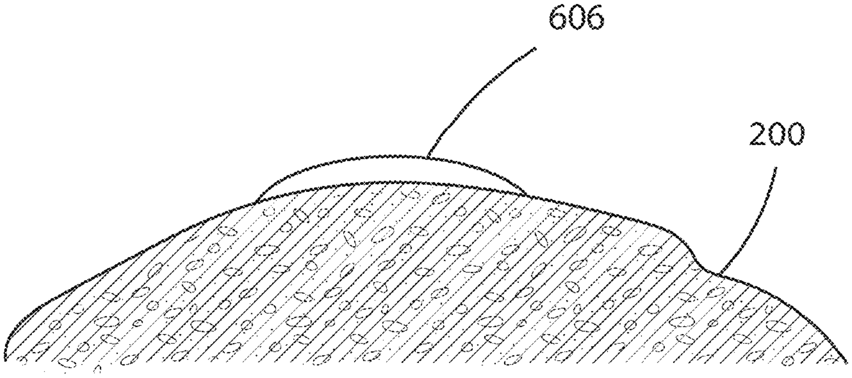
FIGS. 7A to 7C show steps for performing a surgical procedure using a patch according to another embodiment of the disclosure.
Figure 7B:
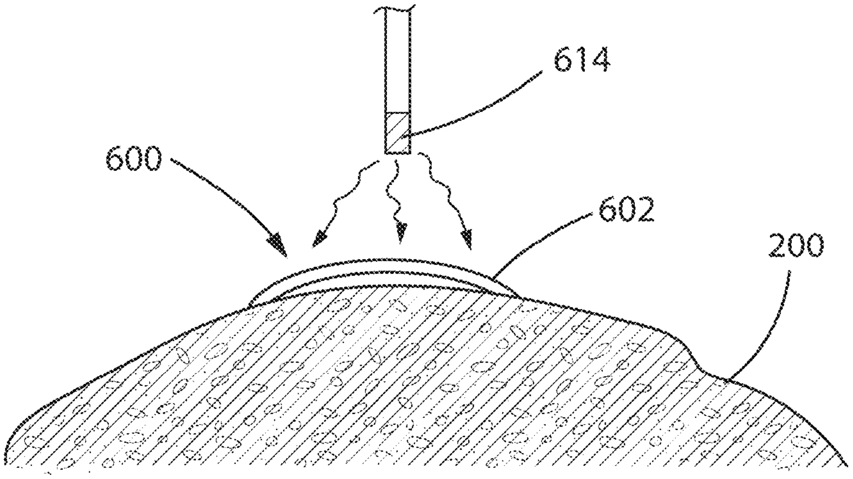

The disclosure is not limited to a curable material 606 formed by two precursors 606*a*, 606*b*, but includes using curable material 606 that is a single component that is cured once it is deposited on the surface of structure 200. As shown in FIG. 7A, single-component, curable material 606 is deposited on structure 200. Curable material 606 may be a substance that can be cured by application of light or heat. According to one embodiment, once the curable material 606 is deposited, an energy source 614 is positioned near structure 200 and actuated to cause the material to cure, or partially cure to form patch 600, as shown in FIG. 7B. According to one embodiment, heat is applied to cure the material by light delivered by a laparoscopic telescope 612, such as those routinely used as part of known laparoscopic procedures. According to another embodiment, the curable material is cured by exposure to light at a selected wavelength, for example, ultraviolet light. Energy source 614 delivers a selected intensity and duration of heat or light to cure material 606 to form patch 600.

According to a further embodiment, prior to applying material 606 to hollow structure 200, as shown in FIG. 6B or 7A, a layer of adhesive, such as an adhesive described in other embodiments, is applied to the structure so that the adhesive is positioned between structure 200 and patch 600. The adhesive may reinforce the bond between patch 600 and the surface of structure 200.

Figure 7C:
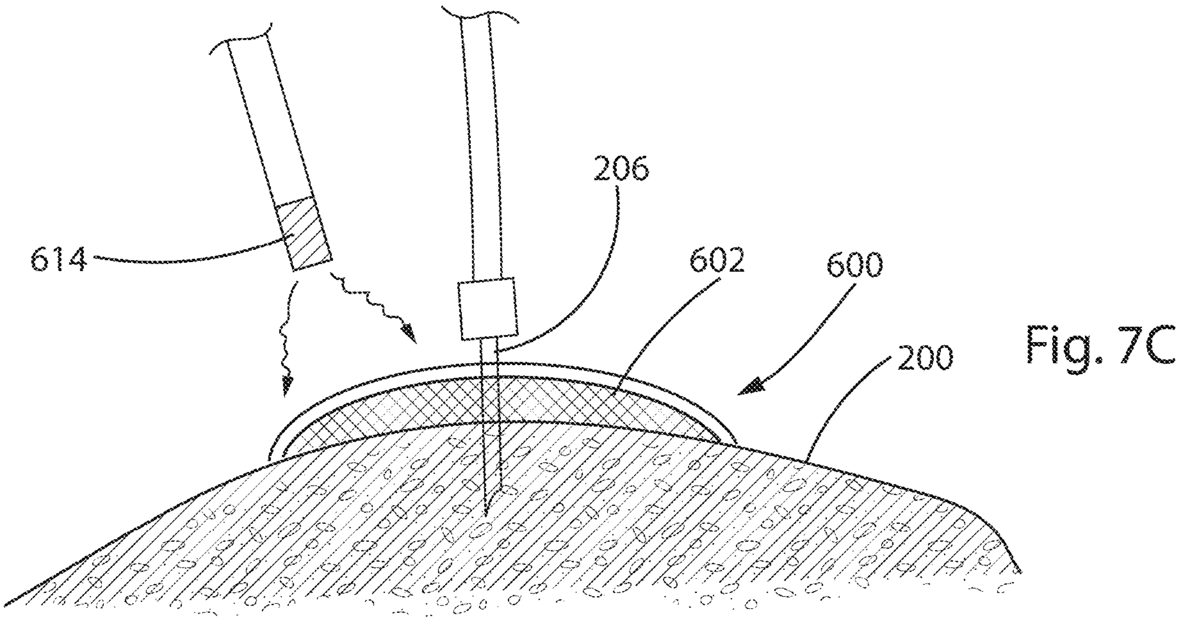

FIGS. 7A-7C show steps for treating hollow structure 200 according to a further embodiment of the disclosure. As shown in FIG. 7A, material 606 is applied to the surface of structure 200. As shown in FIG. 7B, energy source 614 is placed near material 606. Energy source 614 is energized with a selected intensity and duration to form cured layer 602 across the proximal surface of material 606. Energy source 614 is controlled so that material 606 below cured layer 602 remains uncured or is only partially cured. As a result, patch 600 includes a cured elastomeric layer 602 containing an uncured inner volume. As with previous embodiments, hollow needle 206 may be inserted through patch 600 to treat hollow structure 200. Because the inner volume of patch 600 is uncured or only partially cured, it readily conforms to the surface of needle 206, forming a liquid-tight seal around needle 206. When needle 206 is withdrawn from structure 200 and patch 600, the uncured material flows to heal the path where the needle was withdrawn from the patch. According to another embodiment, once needle 206 is withdrawn from patch 600, an additional dose of energy is applied to further cure material 606 to assure that no opening is provided along the path of the needle.

According to a further embodiment shown in FIG. 7C, once needle 206 is inserted through patch 600, one or more additional doses of energy from energy source 614 are applied to cure the material within the inner volume of patch 600. According to one embodiment, this fixes the needle with the patch. During a procedure to dissect and remove structure 200, needle 206 is removed from the patient's body along with structure 200.

According to some embodiments of the disclosure, curable material 606 is selected so that curing or partial curing results in a material with a rubbery, elastomeric consistency. Material 606 may be a single component system or may be formed by two components which mix as they are extruded together, as shown in FIGS. 6A and 6B. According to some embodiments, material 606 is a composite resin including a silane or siloxane backbone with a bound organic moiety, such as methyltriacetoxysilane, a bis-amino silane such as bis(trimethylsilylpropyl)amine, methyl hydrogen polysiloxane, or vinyl oximino silane. According to one embodiment, material 606 is a room temperature vulcanizing (RTV), rapid curing, silicone-based adhesive rubber.

According to a further embodiment, curable material 606 does not form an elastomer, but instead forms a relatively brittle solid, for example, a solidified cyanoacrylate, after being exposed to a curing agent, a light source, or a heat source. Curable material 606 is partially cured, as shown in FIG. 7B, to form cured layer 602, with uncured material forming the bulk of patch 600. Instead of relying on elastomeric properties of layer 602 to form a seal between the needle or cannula and the structure, the uncured material in the interior volume of patch 600 flows around the periphery of needle or cannula 206 to form the seal.

According to other embodiments, curable material 606 is a UV-curable, gel-like acrylic-based composite, such as sobornyl acrylate, and may include elastomeric or polymeric thickeners. According to other embodiments, curable material 606 is a cyanoacrylate-based composite, such as ethyl 2-cyanoacrylate, or an ethyl/octyl monomer combination for added flexibility, that is cured with an activator such as an organic disulphide or sulfenamide.

According to some embodiments, curable material 606 is delivered to the surface of structure 200 as a paste or putty. The paste or putty is spread onto the surface of hollow structure 200 and then cured to form elastomeric patch 600.

According to some embodiments, patch 600 and precursors 606 are formed from bioabsorbable materials. As with some embodiments described above, patch 600 remains in the patient's body following the medical procedure and is absorbed.

Aspects of the disclosure include a device for treating a hollow structure within an organism to remove fluid from or add a fluid to the hollow structure, the device comprising: a main body comprising a thin, fluid-impermeable layer having a distal surface and a proximal surface and including a septum, wherein the septum is adapted to allow a needle to be inserted therethrough and to form a fluid-tight seal around a periphery of the needle; and an adhesive layer disposed on the distal surface of the main body, the adhesive layer surrounding the septum, wherein the adhesive layer is adapted to fix the main body to a surface of the hollow structure and to create a fluid-tight seal between the septum and the hollow structure. According to one aspect the septum is self-sealing. According to another aspect the septum and the main body are contiguous and formed from the same material. According to another aspect one or more of the main body and the septum are formed from an elastomer. According to another aspect one or more of the main body, the septum, and the adhesive layer are bioabsorbable. According to another aspect the adhesive layer comprises one or more of a contact adhesive, a ultraviolet light-cured adhesive, a two-component adhesive, a fibrin-based adhesive, a collagen-based adhesive, a gelatin-based adhesive, an albumin-based adhesive, a chitosan-based adhesive, a chondroitin sulfate-based adhesive, a dextran-based adhesive, a cyanoacrylate adhesive, a polyethylene glycol-based adhesive, a polyurethane-based adhesive, a hydrogel-based adhesive, and a biomimetic adhesive. According to another aspect the main body further comprises one or more tabs protruding from the proximal surface, wherein the one or more tabs are adapted to be grasped by a surgical instrument. According to another aspect the main body is round, oval, square, rectangular, polygonal, or star-shaped. According to another aspect the main body is adapted to be cut to a desired shape during a medical procedure. According to another aspect the main body forms a circle, wherein the septum is located at a center of the circle, wherein the main body has a first thickness at the center and a second thickness at a perimeter of the circle, and wherein the first thickness is greater than the second thickness. According to another aspect the main body has an intermediate thickness between the center and the perimeter. According to another aspect the intermediate thickness varies continuously from the center to the perimeter. According to another aspect the intermediate thickness varies stepwise from the center to the perimeter. According to another aspect the hollow structure is a cyst, a lesion or an organ. According to another aspect the cyst is a hydatid liver cyst and an antiparasitic agent is administered to the cyst by the needle. According to another aspect the hollow structure is a gallbladder, a part of a urinary system, an intestine, or a blood vessel of the organism. According to another aspect a contrast agent is administered to the hollow structure by the needle. According to another aspect the organism is a human or a non-human animal.

Other aspects of the disclosure include a patch to aid in manipulation of a bodily structure while conducting a procedure on a subject, the patch comprising: a main body comprising a distal surface and a proximal surface; one or more extensions, tabs or handles on the proximal surface adapted to be manipulated by a surgical instrument; and an adhesive layer disposed on the distal surface of the main body, wherein the adhesive layer is adapted to fix the main body to a surface of the structure. According to one aspect the main body is formed from an elastomer. According to another aspect one or more of the main body, tabs and the adhesive layer are bioabsorbable. According to another aspect the adhesive layer comprises one or more of a contact adhesive, a ultraviolet light-cured adhesive, a two-component adhesive, a fibrin-based adhesive, a collagen-based adhesive, a gelatin-based adhesive, an albumin-based adhesive, a chitosan-based adhesive, a chondroitin sulfate-based adhesive, a dextran-based adhesive, a cyanoacrylate adhesive, a polyethylene glycol-based adhesive, a polyurethane-based adhesive, a hydrogel-based adhesive, and a biomimetic adhesive. According to another aspect the main body is round, oval, square, rectangular, polygonal, or star-shaped. According to another aspect the main body is adapted to be cut to a desired shape during the procedure. According to another aspect the main body forms a circle wherein the main body has a first thickness at the center and a second thickness at a perimeter of the circle, and wherein the first thickness is greater than the second thickness. According to another aspect the main body has an intermediate thickness between the center and the perimeter. According to another aspect the intermediate thickness varies continuously from the center to the perimeter. According to another aspect the intermediate thickness varies step-wise from the center to the perimeter. According to another aspect the bodily structure is a hollow structure. According to another aspect the bodily structure is a solid structure. According to another aspect the bodily structure is the liver, spleen or kidney. According to another aspect the organism is a human or a non-human animal.

Other aspects of the disclosure include a method of treatment of a hollow structure within an organism to remove fluid from or add a fluid to the hollow structure, the method comprising the steps of: applying a curable material to a surface of the hollow structure; curing or partially curing the curable material to convert at least a portion of the curable material to create a patch, wherein the patch adheres to the surface to create a fluid-tight seal between the patch and the hollow structure, wherein the patch is adapted to allow a needle to be inserted therethrough and to form a fluid-tight seal around a periphery of the needle. According to one aspect the curable material comprises two or more precursors, wherein the step of curing comprises mixing the precursors, wherein the precursors react to convert the curable material to an elastomer. According to another aspect the two or more precursors comprise a liquid silicone rubber and a curing agent. According to another aspect the two or more precursors comprise one or more of a two-part silicone based adhesive rubber system, a room temperature vulcanizing (RTV) silicone-based adhesive rubber, a rapid curing, silicone-based adhesive rubber, a composite resin including a silane or siloxane backbone with a bound organic moiety that includes methyltriacetoxysilane, a bis-amino silane including bis(trimethylsilylpropyl)amine, methyl hydrogen polysiloxane, or vinyl oximino silane. According to another aspect the curable material comprises a light-curable substance and wherein the step of curing or partial curing comprises exposing to the curable material applied to the surface with light at a selected wavelength. According to another aspect the step of exposing comprises directing light from a light source energized with a selected intensity or a selected duration to fully cure the elastomer, wherein an inner volume of the patch is cured. According to another aspect the step of exposing comprises energizing a light source with a selected intensity or a selected duration to partially cure the curable material to form the elastomer across a proximal surface of the elastomeric patch, wherein at least a portion of an inner volume of the patch remains uncured. According to another aspect, the method includes the step of inserting the needle through the elastomeric patch and into the hollow structure, wherein the periphery of the needle is in contact with the curable material in the inner volume. According to another aspect, the method includes the step of further curing the curable material within the inner volume of the patch, wherein the elastomer is formed in the inner volume along the periphery of the needle. According to another aspect the method includes the step of removing the needle from the hollow structure and the elastomeric patch along a needle path; and further curing the curable material within the inner volume of the patch along the needle path. According to another aspect the curable material is a liquid, a gel, or a paste. According to another aspect, once the needle or cannula is withdrawn from the structure, an additional layer of curable material is applied to the patch and then cured to assure that any opening left by the needle is fully closed. The additional layer may extend beyond the periphery of patch to enhance the seal between the patch and the surface of structure. According to another aspect prior to the step of applying the curable material to the surface of the hollow structure, the method comprises the step of depositing an adhesive layer on the surface, wherein, in the step of applying the curable material is applied to a proximal surface of the adhesive layer. According to another aspect the adhesive layer comprises one or more of a contact adhesive, a ultraviolet light-cured adhesive, a two-component adhesive, a fibrin-based adhesive, a collagen-based adhesive, a gelatin-based adhesive, an albumin-based adhesive, a chitosan-based adhesive, a chondroitin sulfate-based adhesive, a dextran-based adhesive, a cyanoacrylate adhesive, a polyethylene glycol-based adhesive, a polyurethane-based adhesive, a hydrogel-based adhesive, and a biomimetic adhesive. According to another aspect the hollow structure is a cyst, a lesion or an organ. According to another aspect the cyst is a hydatid liver cyst, and an antiparasitic agent is administered to the cyst by the needle. According to another aspect the hollow structure is a gallbladder, a part of a urinary system, an intestine, or a blood vessel of the organism. According to another aspect the method includes the step of delivering a contrast agent administered to the hollow structure by the needle. According to another aspect the organism is a human or a non-human animal.

Other aspects of the disclosure include a device for treating a hollow structure within an organism to remove fluid from or add a fluid to the hollow structure, the device comprising: a main body comprising a thin, fluid-impermeable layer having a distal surface and a proximal surface, wherein the main body is formed by applying a curable material to a surface of the hollow structure and curing the material to form a patch on the surface, wherein the patch is adapted to allow a needle to be inserted therethrough and to form a fluid-tight seal around a periphery of the needle.

While illustrative embodiments of the disclosure have been described and illustrated above, it should be understood that these are exemplary of the disclosure and are not to be considered as limiting. Additions, deletions, substitutions, and other modifications can be made without departing from the spirit or scope of the disclosure. Accordingly, the disclosure is not to be considered as limited by the foregoing description.

The invention claimed is:

1. A device for treating a hollow structure within an organism to remove fluid from or add a fluid to the hollow structure, the device comprising:

a main body comprising a thin, fluid-impermeable layer having a distal surface and a proximal surface and including a septum, wherein the septum is adapted to allow a needle to be inserted therethrough and to form a fluid-tight seal around a periphery of the needle, wherein the fluid is removed or added via the needle; and an adhesive layer disposed on the distal surface of the main body, the adhesive layer surrounding the septum, wherein the adhesive layer is adapted to fix the main body to a surface of the hollow structure and to create a fluid-tight seal between the septum and the hollow structure.

2. The device of claim 1, wherein the septum is self-sealing.

3. The device of claim 1, wherein the septum and the main body are contiguous and formed from the same material.

4. The device of claim 1, wherein one or more of the main body and the septum are formed from an elastomer.

5. The device of claim 1, wherein one or more of the main body, the septum, and the adhesive layer are bioabsorbable.

6. The device of claim 1, wherein the adhesive layer comprises one or more of a contact adhesive, a ultraviolet light-cured adhesive, a two-component adhesive, a fibrin-based adhesive, a collagen-based adhesive, a gelatin-based adhesive, an albumin-based adhesive, a chitosan-based adhesive, a chondroitin sulfate-based adhesive, a dextran-based adhesive, a cyanoacrylate adhesive, a polyethylene glycol-based adhesive, a polyurethane-based adhesive, a hydrogel-based adhesive, and a biomimetic adhesive.

7. The device of claim 1, wherein the hollow structure is a cyst, a lesion, a gallbladder, a part of a urinary system, an intestine, a blood vessel or another organ.

8. The device of claim 7, wherein the cyst is a hydatid liver cyst, the device further comprising an antiparasitic agent administered to the cyst by the needle.

9. The device of claim 1, further comprising a contrast agent administered to the hollow structure by the needle.

10. A device for treating a hollow structure within an organism to remove fluid from or add a fluid to the hollow structure, the device comprising:

a main body comprising a thin, fluid-impermeable layer having a distal surface and a proximal surface and including a septum, wherein the septum is adapted to allow a needle to be inserted therethrough and to form a fluid-tight seal around a periphery of the needle; and an adhesive layer disposed on the distal surface of the main body, the adhesive layer surrounding the septum, wherein the adhesive layer is adapted to fix the main body to a surface of the hollow structure and to create a fluid-tight seal between the septum and the hollow structure, and wherein the main body further comprises one or more tabs protruding from the proximal surface, wherein the one or more tabs are adapted to be grasped by a surgical instrument.

11. A device for treating a hollow structure within an organism to remove fluid from or add a fluid to the hollow structure, the device comprising:

a main body comprising a thin, fluid-impermeable layer having a distal surface and a proximal surface and including a septum, wherein the septum is adapted to allow a needle to be inserted therethrough and to form a fluid-tight seal around a periphery of the needle; and an adhesive layer disposed on the distal surface of the main body, the adhesive layer surrounding the septum, wherein the adhesive layer is adapted to fix the main body to a surface of the hollow structure and to create a fluid-tight seal between the septum and the hollow structure, and wherein the main body forms a circle, wherein the septum is located at a center of the circle, wherein the main body has a first thickness at the center and a second thickness at a perimeter of the circle, and wherein the first thickness is greater than the second thickness.

12. The device of claim 11, wherein the main body has an intermediate thickness that is constant or that varies continuously or stepwise between the center and the perimeter.

* * * * *